(12) United States Patent
Lehtinen et al.

(10) Patent No.: US 6,324,926 B1
(45) Date of Patent: Dec. 4, 2001

(54) METHOD AND DEVICE FOR TAKING A SAMPLE FROM A CLOSED TEST TUBE

(75) Inventors: Kauko Lehtinen, Raisio; Markku Ojala; Antero Martinmäki, both of Turku, all of (FI)

(73) Assignee: Innotrac Diagnostisc Oy, Turku (FI)

( * ) Notice: Subject to any disclaimer, the term of this patent is extended or adjusted under 35 U.S.C. 154(b) by 0 days.

(21) Appl. No.: 09/394,105

(22) Filed: Sep. 13, 1999

(30) Foreign Application Priority Data

Sep. 14, 1998 (FI) ....................................................... 981964

(51) Int. Cl.⁷ .................................................. G01N 35/00
(52) U.S. Cl. ..................... 73/864.24; 73/864.74; 141/330
(58) Field of Search ........................... 73/863.85, 864.86, 73/864.87, 864.24, 864.74, 863.83; 141/329, 330; 600/575, 576, 577, 578, 579

(56) References Cited

U.S. PATENT DOCUMENTS

| 3,159,159 | * | 12/1964 | Cohen .................................. 600/579 |
| 3,706,305 | * | 12/1972 | Berger et al. .......................... 600/575 |
| 4,758,409 | * | 7/1988 | Uffenheimer ....................... 73/864.51 |
| 4,928,539 | * | 5/1990 | Champseix et al. ............... 73/864.24 |
| 5,151,184 | * | 9/1992 | Ferkany ................................. 210/514 |
| 5,934,885 | * | 8/1999 | Farrell et al. ......................... 417/392 |
| 5,935,523 | * | 8/1999 | McCandless et al. ............ 73/864.24 |

* cited by examiner

Primary Examiner—Hezron Williams
Assistant Examiner—Michael Cygan
(74) Attorney, Agent, or Firm—Kubovcik & Kubovcik

(57) ABSTRACT

A method for taking a sample from a closed test tube without removing the stopper of the test tube. According to the method, the stopper of the test tube is pierced with a disposable piercing needle through which the sample is taken to the sample receptacle of the sampling device. From there the sample is dispensed with a dispenser needle. The sampling device comprises an adapting element for fitting the test tube, with the piercing needle first, to the sampling device, a cup-like sample receptacle and a suction device for drawing the sample that is in the test tube into the sample receptacle.

5 Claims, 5 Drawing Sheets

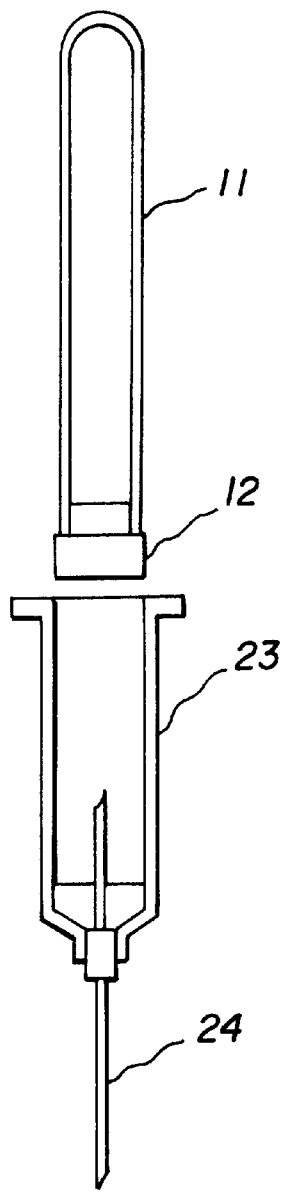
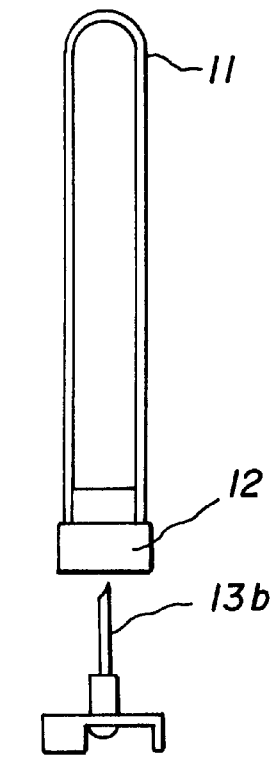
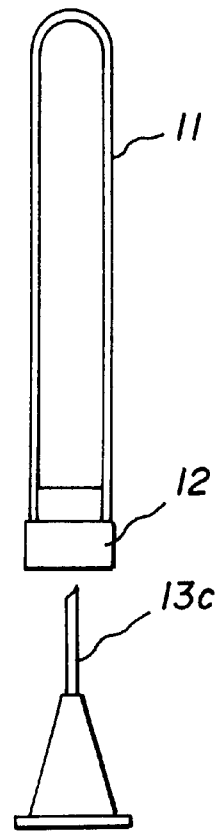
FIG. 3
FIG. 4
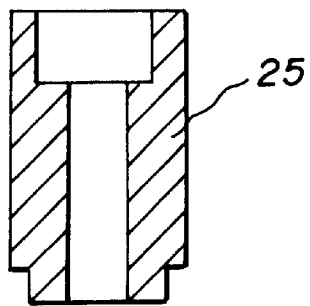
FIG. 2

METHOD AND DEVICE FOR TAKING A SAMPLE FROM A CLOSED TEST TUBE

The object of the invention is a method for taking a sample from a closed test tube without removing the stopper of the test tube, according to which method the stopper of the test tube is pierced with a needle, through which at least part of the sample is taken out of the test tube.

PRIOR ART

Today blood samples are taken with so-called vacuum specimen tubes, which are provided with a stopper on top that automatically closes the tube hygienically. However, many blood analyzers require the stopper to be removed when the sample is taken to the analyzer, which is an unhygienic and undesirable procedure. Removing the stopper also complicates further handling of the blood tube, such as transfer elsewhere, for example. Therefore, the stopper is often put back onto the tube. This in turn leads to the risk of the stoppers being mixed up.

To eliminate this problem, various methods have been developed for taking the amount of the sample required by the analyzer from the tube without having to remove its stopper. These methods have not, however, proved useful either due to their laboriousness or unreliability. Therefore, the aim of the present invention is to obtain a new method, which does not have the disadvantages of the known methods.

Method Relating to the Invention

It is characteristic of the method relating to the invention that the stopper of the test tube is pierced with a piercing needle, through which at least part of the sample is taken out of the test tube into a sample receptacle, from which the sample is dispensed with a dispenser needle or the like.

According to the invention, the user may pierce the stopper using different kinds of disposable needles used for piercing stoppers, and thereafter, by a simple pushing movement, take the amount of sample required by the analyzer by means of an automatic suction system relating to the invention. After this the specimen tube is immediately free for use for any other tests.

The invention presented here achieves the aim of not having to remove the stopper. In addition, it differs from the used solutions, among other things, as regards the following:

1. In it the stopper is not pierced with the spike used for the actual dispensing, in which case it is not subject to strong physical strain while penetrating through the stopper. In such case the spike can be thinner, coated to ensure the lowest possible carry-over, and shaped as required for accurate dispensing, i.e. flat-topped.
2. It makes use of disposable needles, which are used in any case for blood sampling, for example, in which case, without producing additional waste, a situation is obtained where the needle that has penetrated through the stopper and has been in close contact with blood is discarded after use and there is no risk that the next sample might be affected.

Embodiments of the Method

The sample receptacle relating to the invention can also be used as a dilution dish.

Device Relating to the Invention

Another object of the invention is a device for taking a sample from a closed specimen tube. It is characteristic of a device relating to the invention that the sampling device comprises a dish inside which there is a cup-like sample receptacle for the sample in the test tube, an adapting element for fitting the test tube to the sampling device, with the piercing needle first, and a suction device for drawing the sample in the test tube into the sample receptacle.

In a device relating to the invention, when the user presses the specimen tube against the sealing ring, the required amount of the sample is drawn into the sample receptacle, after which the specimen tube is removed. The desired doses of the sample are taken from the sample receptacle with the sample dispenser, after which the sample receptacle and the spike of the sample dispenser are washed in a joint washing procedure.

Embodiment of the Device

Different kinds of adapters can be attached to the device relating to the invention, in which case the needles that are used can be almost any kind of needles.

Examples of Embodiments

In the following, the invention is described using examples with reference to the accompanying drawings, in which

LIST OF FIGURES

FIG. 1 shows a section of an embodiment of the device relating to the invention, as seen from the side.

FIG. 2 shows the test tube and the needle holder and adapter to be attached to it, as seen from the side.

FIG. 3 corresponds to FIG. 2 and shows the test tube and a second type of a needle.

FIG. 4 corresponds to FIG. 2 and shows the test tube and a third type of a needle.

FIG. 5 corresponds to FIG. 1 and shows the device and the adapter for attaching the needle holder to the device.

FIG. 6 corresponds to FIG. 1 and shows the device according to another embodiment of the invention.

FIG. 7 shows a section of the device of FIG. 6 seen from above.

FIG. 8 shows a section of an adapter according to another embodiment.

DESCRIPTION OF THE FIGURES

FIG. 1 shows the sampling device 10 and a test tube 11 placed on it. The test tube is a so-called vacuum specimen tube, which is sealed tight and hygienically with a stopper 12. The test tube 11 contains, for instance, a blood sample 22a.

The stopper 12 on the end of the vacuum specimen tube 11 is a rubber cap, which is pierced with a needle 13 before taking the blood sample 22a. When the needle 13 has pierced the rubber cap 12, the vacuum is released from the test tube 11. In FIG. 1 the needle 13 has only been shown diagrammatically as a thin tube piercing the rubber cap 12, because the needle can be of any known type of needle or separately designed for this purpose. The essential thing is that a hole is formed by the needle 13 in the stopper formed by the rubber cap 12, from where and through which the blood sample 22a can be taken. The needle 13 is left in its place in the stopper 12 during sampling.

Figure 1:
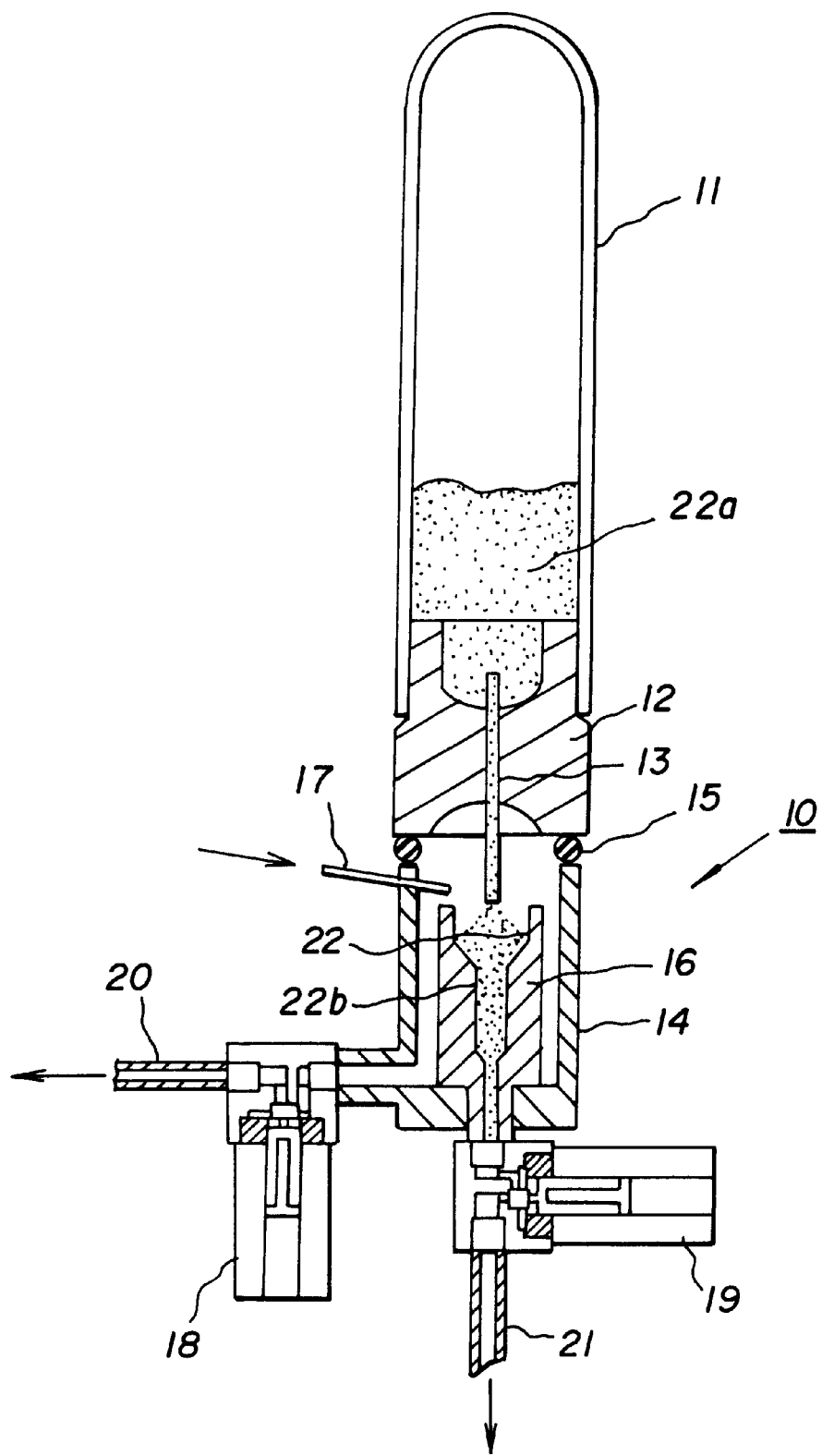

The sampling device 10 comprises a dish 14 and, inside it, a cup-like sample receptacle 16. The sample receptacle 16 has a recess, into which some of the sample 22a in the test tube 11 is transferred. In addition, in the lower part of the sampling device 10 there are two tubes 20 and 21, to which valves 18 and 19 have been attached. The tubes 20 and 21 have at one end been connected to a waste container that is under vacuum, not shown in FIG. 1. In the sampling device 10 the tube 20 has been taken to the bottom of the dish 14, to the space between the dish 14 and the sample receptacle 16. The tube 21 in turn has been connected to the bottom of the cup of the sample receptacle 16.

When sampling from the test tube 11 is started, the test tube 11 is placed on the sampling device 10. In this case the cap 12 of the test tube 11 is pressed against the edge of the dish 14 of the sampling device 10 and is sealed tightly against it by means of the edge sealing 15. Sampling from the test tube 11 is started automatically when the pressure sensor or other switching element that is part of the sampling device 10 registers that the test tube 11 is in its place. These devices are not shown in FIG. 1.

When the test tube 11 is tightly in its place against the edge sealing 15 of the dish 14 of the sampling device 10, the first valve 18 of the sampling device 10 is opened. In this case the valve 18 opens the tube 20 leading from the bottom of the dish 14 to the waste container, which is under vacuum. The vacuum formed in the sampling device 10 now draws the sample 22a in the test tube 11 into the cup-like sample receptacle 16 of the sampling device 10. The sample transferred to the sample receptacle 16 is marked with reference number 22b in FIG. 1. After this the valve 18 of the sampling device 10 is closed and the test tube 11 with its needle 13 is removed from the sampling device 10.

The sampling device 10 is then open at its top, in which case the sample 22b, which has been transferred into the cup of the sample receptacle 16 can be transferred further, using, for example a pipetting needle into the sample cup of the device that measures the sample. The pipetting needle and measuring devices are not shown in FIG. 1. When the sample 22b has thus been removed from the sampling device 10, in the sampling device, the other valve 19 of the device 10 is opened, which opens the tube 21 leading from the bottom of the cup of the sample receptacle 16 into the waste container, which is under vacuum. In this case vacuum draws the excess sample fluid 22b, i.e. sample fluid that remains at the bottom of the cup of the sample receptacle 16, into the waste container.

After the sampling device 10 has been emptied in this way, the pipetting needle is brought back above the sample receptacle 16 of the sampling device 10. The spraying of washing fluid now starts from the pipetting needle into the sample receptacle 16 of the sampling device 10. Then the cup of the sample receptacle 16 is filled first, and washing liquid also flows over into the dish 14 that is outside the sample receptacle.

Washing of the sample receptacle 16 and the dish 14 of the sampling device 10 is carried out by alternately opening the valves 18 and 19. Correspondingly, they open alternately the connections into the waste container via the tubes 20 and 21. When the first valve 18 is opened the space between the sample receptacle 16 and the dish 14 is emptied of fluid. Correspondingly, when the valve 18 is closed and the other valve 19 of the sampling device 10 is opened, the cup of the sample receptacle 16 is emptied. In this way both the dish of the sampling device 10 and the cup of the sample receptacle 16 are alternately emptied of and filled with washing liquid. Washing continues as long as new washing liquid is fed from the pipetting needle into the sampling device 10. Washing continues in the way described above, by alternately opening both valves 18 and 19.

Embodiments

The sample receptacle 16 of the sampling device 10 can also be used as a dilution dish for the sample 22b. In this case the intermediate washing liquid is introduced into the cup of the sample receptacle 16 through the tube 17 that is connected to the wall of the dish 14.

The sample 22b can also be brought into the cup of the sample receptacle 16 either by a capillary tube or pipette.

Adapters

The needle 13 shown in FIG. 1 can be almost any known type of needle. Different adapters can be produced for them.

FIG. 2 shows examples of adapters, in which case very different test tubes are suitable for using with the device 10.

FIG. 2 shows a Venoject-type needle holder 23 that is used in connection with the test tube 11, which needle holder comprises an injection needle 24. When a needle holder 23 of this kind is used in connection with the device 10, an adapter 25 is used between them.

FIG. 3 shows a Diff-safe type needle 13b used for piercing the cap 12 of the test tube 11. Correspondingly, FIG. 4 shows a Terumo needle 13c, which is suitable for this purpose.

Figure 5:
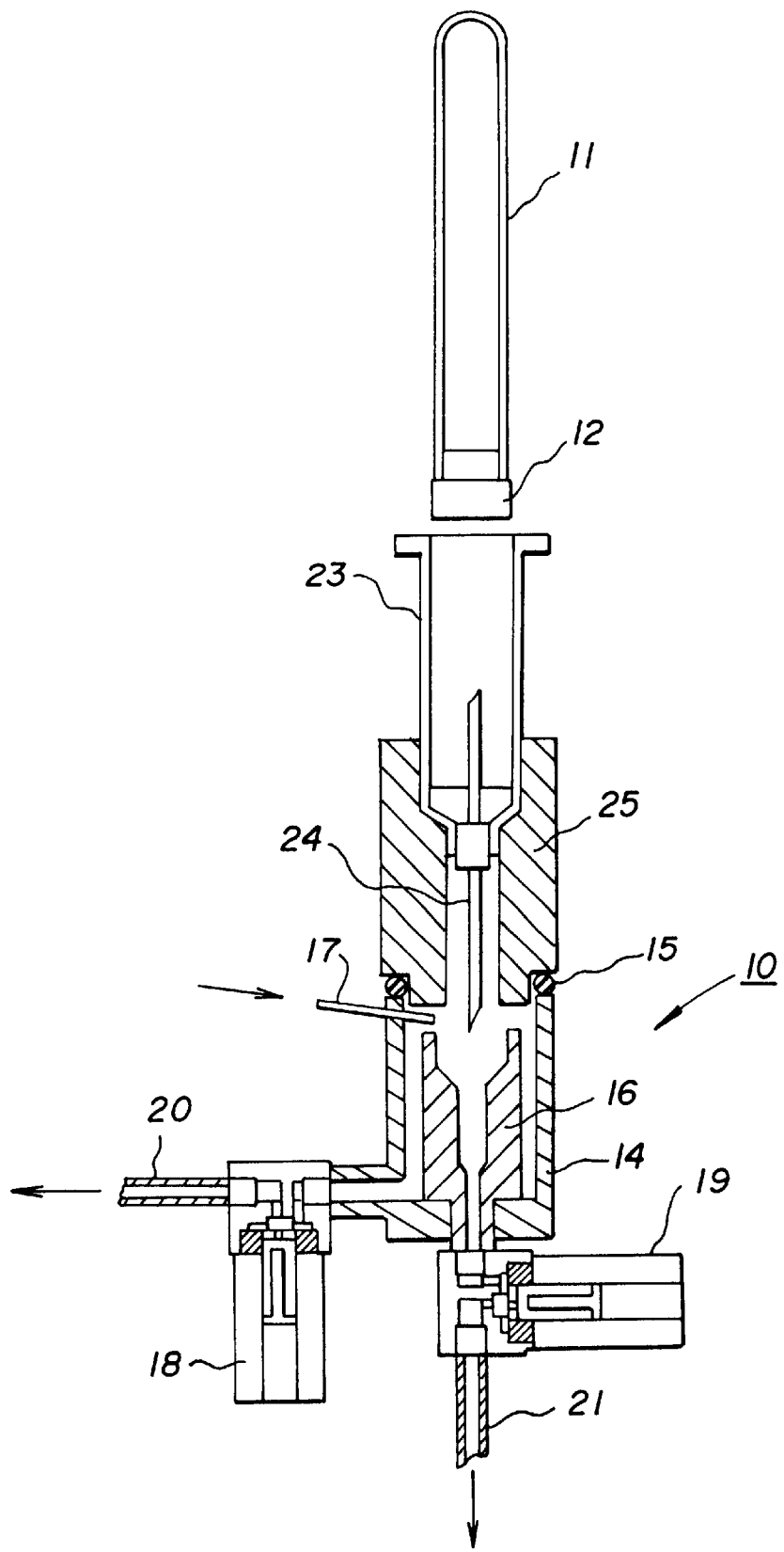

FIG. 5 shows a device 10, which corresponds to the device in FIG. 1 and which comprises an adapter 25 for attaching the needle holder 23 to the edge of the dish 14. There is sealing 15 between the adapter 25 and the edge of the dish 14. By using the adapter the needle 24 is positioned at the correct distance from the sample receptacle 16 in the device 10.

Figure 6:
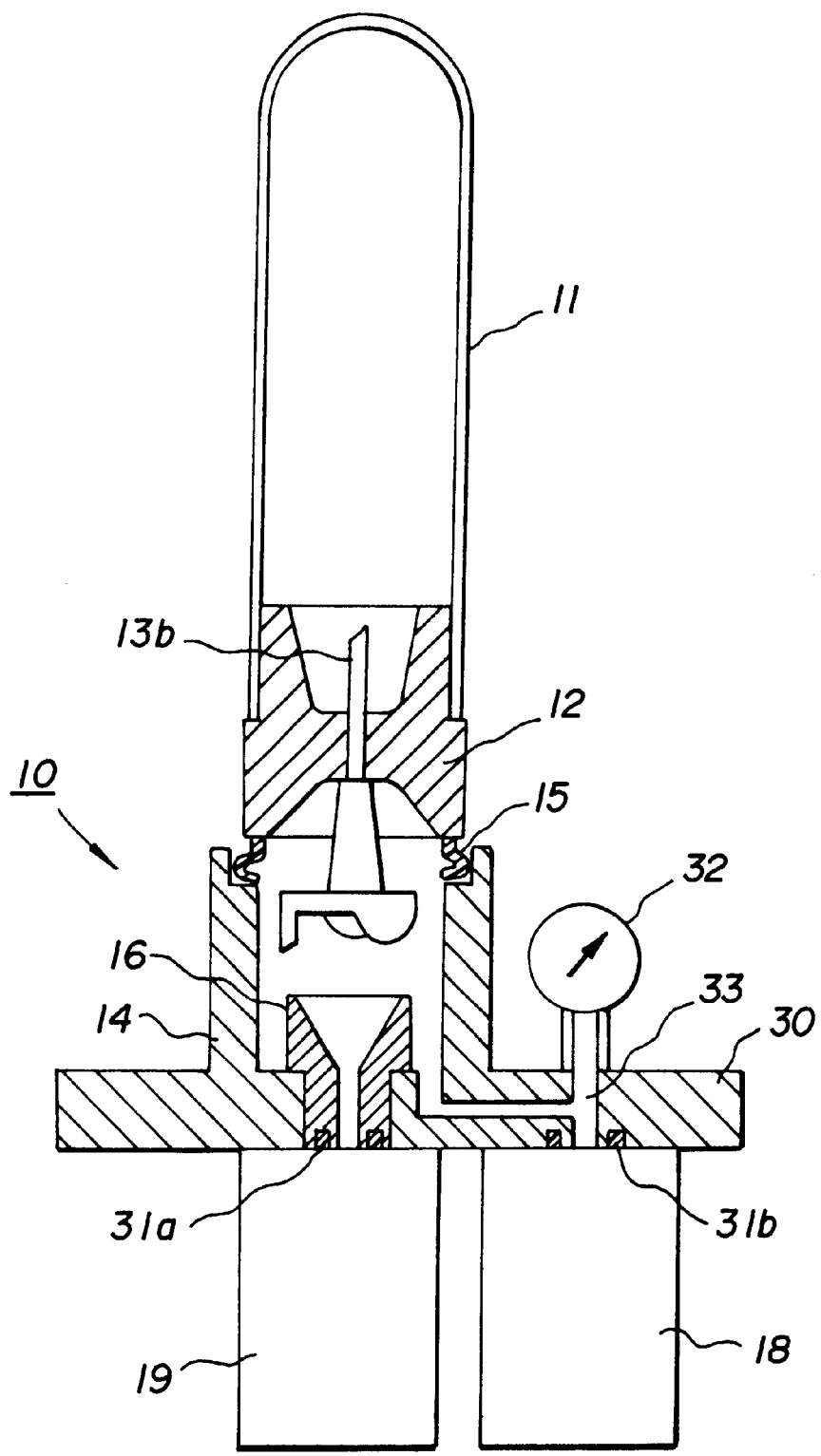

In FIG. 6 the base 30 of the device 10 is a plate, under which the valves 18 and 19 have been attached. The liquid canals have been formed into the plate 30. In FIG. 6 the canal 33, which is connected to the valve 18, is equipped with a pressure gauge 32 or with a pressure sensor. When the test tube 11 will be pressed against the edge sealing 15 of the dish 14 of the sampling device 10, the pressure gauge 32 registers the pressure change. This is a signal to the device 10 that the test tube 11 has been placed in to its place and then the device 10 can start sampling. The pressure gauge 32 can also be used for making a leak test for the edge sealing 15.

Figure 7:
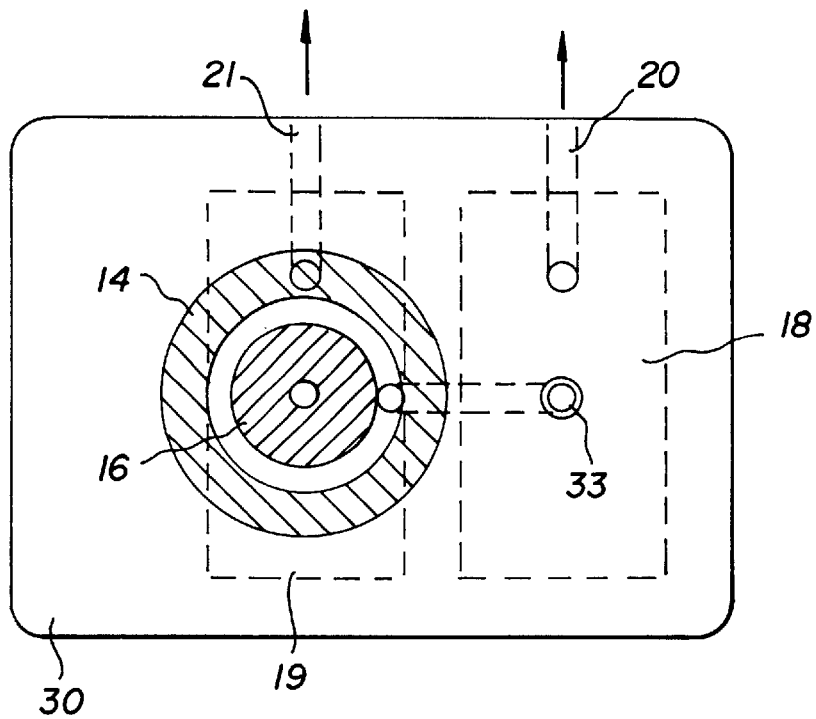

In FIG. 7 the sampling device 10 of FIG. 6 is seen from above. The dish 14 and the sample receptacle 16 are described in a section. A canal from the center of the sample receptacle 16 is leading to the valve 19, from which a canal 21 is leading into the waste container. From the bottom of the dish 14, in the space between the dish 14 and the sample receptacle 16 a canal is leading to the valve 18. Into that canal 33 a pressure gage is attached. The canal 20 from the valve 18 is also leading into a waste container.

Figure 8:
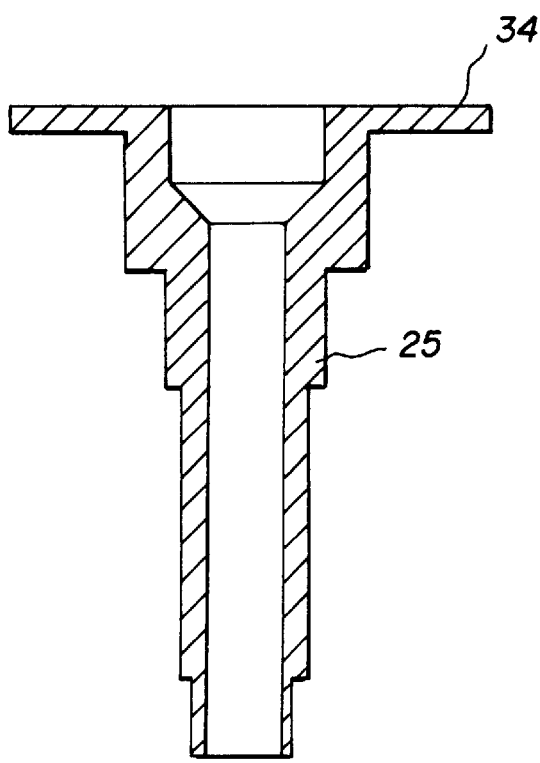

In FIG. 8 there is another adapter 25, which has a larger flange 34 in order to protect the user and to prevent accidental needle shots.

It is obvious to a person skilled in the art that the different embodiments of the invention may vary within the scope of the claims presented below.

What is claimed is:

1. A device for taking a sample from a closed test tube, characterized in that the sampling device comprises a dish, inside of which there is a cup-like receptacle for the sample in the test tube, an adapting element for fitting the test tube to the sampling device, with a piercing needle through which the sample is taken first, and a suction device for drawing the sample in the test tube into the sample receptacle.

2. A device as claimed in claim 1, characterized in that the adapting element of the sampling device has a sealing ring, which has been attached to a starting device so that the suction device starts when the user presses the test tube against the sealing ring of the sampling device.

3. A device as claimed in claim 1, characterized in that the sample receptacle of the sampling device has been connected to a waste container under vacuum by a tube equipped with a valve.

4. A device as claimed in claim 1, characterized in that the dish of the sampling device has been connected to a waste container under vacuum by two tubes, which have valves, in that the first tube has been taken to the bottom of the container and the second tube has been connected to the bottom of the cup of the sample receptacle.

5. A device as claimed in claim 1, characterized in that the sampling device comprises an adapter that is between the test tube and the dish of the sampling device, through which adapter the piercing needle of the test tube is placed at the desired distance from the sample receptacle.

* * * * *

UNITED STATES PATENT AND TRADEMARK OFFICE
CERTIFICATE OF CORRECTION

PATENT NO. : 6,324,926 B1  
DATED : December 4, 2001  
INVENTOR(S) : Kauko Lehtinen et al.

Page 1 of 1

It is certified that error appears in the above-identified patent and that said Letters Patent is hereby corrected as shown below:

<u>Title page,</u>
Item [73] Assignee: "Innotrac Diagnostisc Oy" should be -- Innotrac Diagnostics Oy --

<u>Column 4,</u>
Line 45, "15." should be -- 15. In Figure 6, 31a and 31b are O-rings that seal the connections between the canals and the valves 18 and 19. --

Signed and Sealed this

Twenty-first Day of May, 2002

Attest:

Attesting Officer

JAMES E. ROGAN  
Director of the United States Patent and Trademark Office